(12) United States Patent
Netherly et al.

(10) Patent No.: US 6,171,304 B1
(45) Date of Patent: Jan. 9, 2001

(54) METHOD AND APPARATUS FOR CONTROLLING CONTACT OF BIOMEDICAL ELECTRODES WITH PATIENT SKIN

(75) Inventors: Samuel G. Netherly, Afton; Orlin B. Knudson, Vadnais Heights, both of MN (US)

(73) Assignee: 3M Innovative Properties Company, St, Paul, MN (US)

( * ) Notice: Under 35 U.S.C. 154(b), the term of this patent shall be extended for 0 days.

(21) Appl. No.: 09/256,022

(22) Filed: Feb. 23, 1999

Related U.S. Application Data

(63) Continuation-in-part of application No. 08/832,835, filed on Apr. 4, 1997, now abandoned.

(51) Int. Cl.[7] .................................................. A61B 17/39
(52) U.S. Cl. ................. 606/32; 606/35; 607/152
(58) Field of Search ........................ 606/32, 35; 607/142, 607/149, 152, 153, 8; 128/908; 600/547

(56) References Cited

U.S. PATENT DOCUMENTS

| | | | |
|---|---|---|---|
| 4,200,104 | 4/1980 | Harris | 128/303 |
| 4,231,372 | 11/1980 | Newton | 128/303.14 |
| 4,416,276 | 11/1983 | Newton et al. | 128/303.13 |
| 4,416,277 | 11/1983 | Newton | 128/303.13 |
| 4,524,087 | 6/1985 | Engel | 427/2 |
| 4,539,996 | 9/1985 | Engel | 128/640 |
| 4,848,335 | 7/1989 | Manes | 128/303.13 |
| 4,848,353 | 7/1989 | Engel | 128/640 |
| 5,012,810 | 5/1991 | Strand | 128/640 |
| 5,080,099 | 1/1992 | Way et al. | 128/640 |
| 5,087,257 | 2/1992 | Farin et al. | 606/35 |
| 5,196,008 | 3/1993 | Kuenecke et al. | 606/35 |
| 5,215,087 | 6/1993 | Anderson | 128/640 |
| 5,232,838 | 8/1993 | Nelson et al. | 435/30 |
| 5,362,420 | 11/1994 | Itoh et al. | 252/500 |
| 5,372,596 | 12/1994 | Klicek et al. | 606/35 |
| 5,480,399 | 1/1996 | Hebborn | 606/35 |
| 5,688,269 | 11/1997 | Newton et al. | 606/46 |
| 5,797,902 | * 8/1998 | Netherly | 606/32 |
| 5,830,212 | 11/1998 | Cartmell et al. | 606/35 |
| 5,836,942 | 11/1998 | Netherly et al. | 606/32 |
| 5,947,961 | * 9/1999 | Netherly | 606/32 |
| 6,007,532 | * 12/1999 | Netherly | 606/32 |

FOREIGN PATENT DOCUMENTS

| | | |
|---|---|---|
| 32 06 947A | 9/1983 | (DE) . |
| 2 516 782 | 5/1983 | (FR) . |
| WO 81/01954 | 7/1981 | (WO) . |
| WO 96/19152 | 6/1996 | (WO) . |

OTHER PUBLICATIONS

Derwent Abstract for FR 2 516 782 A.

* cited by examiner

*Primary Examiner*—Linda C. M. Dvorak
*Assistant Examiner*—David M. Ruddy
(74) *Attorney, Agent, or Firm*—Robert M. Sprague (57) ABSTRACT

A method of monitoring the contact of a biomedical electrode to skin of a patient is disclosed, where the phase angle of current flow through one portion of the electrode is compared to the phase angle of current flow through another portion of the electrode. The two portions are both electrical conductors, one having a lossy dielectric surface and the other bare metal. Any monitoring of an electrical interface is possible based on the difference in phase angle. Lift of any portion of the electrode from contact with skin of a patient can be monitored more easily than using conventional Contact Quality Monitoring circuitry and "split plate patient plates."

20 Claims, 4 Drawing Sheets

METHOD AND APPARATUS FOR CONTROLLING CONTACT OF BIOMEDICAL ELECTRODES WITH PATIENT SKIN

This application is a continuation in part of Ser. No. 08/832,835 filed Apr. 4, 1997 now abandoned.

FIELD OF INVENTION

This invention concerns a method and apparatus for controlling use of biomedical electrodes, particularly dispersive return electrodes or "patient plates" having lossy dielectric properties, during delivery of electrical current to a patient, particularly during electrosurgery. More particularly, the invention concerns a method of determining whether an electrosurgical patient plate has accidentally lifted in any location from a patient's skin.

BACKGROUND OF INVENTION

Biomedical electrodes are used in a variety of applications and are configured to operate according to the size, type, and direction of current flowing into or out of a body of a patient.

Dispersive electrodes are used in electrosurgery. In modern surgical practice, there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

Unfortunately, any geometry of the large surface area has an edge and perhaps distinct corners or junctions where "edge effects", caused by increased current density at those locations, can have a maximum temperature rise during usage by the patient making such dispersive electrode or cardiac stimulating electrode most uncomfortable to the patient.

The same difficulties concerning edge effect also are present in cardiac stimulating electrodes, such as those used for defibrillation, external pacing, or cardioversion. For a patient already in some discomfort or ill health, pain sensed by the very medical device intended to treat the patient is disconcerting at best.

Safety systems for the electrosurgical patient plates use "Contact Quality Monitor" ("CQM") circuits. All CQM systems currently in use are based on a single design, involving the use of a split patient plate. The reason that the plate must be split is to create two separate conductors that are not electrically joined, unless the electrode is placed on the skin of a patient. If it is indeed properly placed, then a small current can be passed by the generator down one wire of the cable connecting the generator to one of the conductors on the split plate. From there, the current then passes into the flesh of the patient, crosses over to the other conductor of the split plate, and then back through the other wire of the connecting cable to the generator. By analyzing this current, the generator is able to measure an impedance for the combined circuit of the cable, both halves of the split plate, and the patient.

This impedance must be within a certain pre-determined range which assures that the plate has been placed on the patient and that it is in full or nearly full contact with the skin of the patient.

One other point should be made about these CQM systems, and the current that is used by them to determine when the plate is in good contact with the patient: The CQM current should not be confused with the surgical current, which does all the cutting and coagulating. The CQM current is a lower frequency (typically about 39–350 KHz) than the surgical current frequency (typically about 500–1000 KHz), and is hundreds of times smaller in both voltage and amperage than the surgical current (about 1 mV and 1 mA vs. about 500 V and 2 A, respectively).

It is also important to note that the CQM system is only active when the surgical current is not flowing, since the surgical current is so powerful that it would burn out the CQM circuit if the CQM circuit were active while the surgical current was flowing.

The CQM system, first introduced in 1984, has become the industrial safety standard for electrosurgery. Further disclosure of the CQM system is found in U.S. Pat. Nos. 4,200,104 (Harris); 4,231,372 (Newton); 4,416,277 (Newton et al.); 4,416,276 (Newton et al.); and 4,848,335 (Manes).

In addition to the CQM system, additional systems have been developed. One of them is the "NESSY" system sold by Erbe, Inc. of Tüibingen, Germany. The system has two separate circuits, with the first circuit being the standard CQM type described above. The second circuit, however, is unique to the Erbe generator and actually measures the surgical current that is flowing through both halves of the split plate. The amperage flowing in the two halves of the plate is compared, and if there is too great a difference between the current levels the generator will alarm and shut down.

Another attempt to provide protection for an electrosurgery patient is disclosed in U.S. Pat. No. 5,080,099 (Way et al.). In these patents are disclosed a triple plate electrode in order to provide a measure of "peel back" of the patient plate from the patient. But these electrodes disclosed in the Way et al. patent were quite complex to manufacture and use.

SUMMARY OF INVENTION

The present invention determines whether an electrosurgical patient plate has accidentally lifted from a patient's skin. This method is an unexpected and significant improvement over the sensitivity and accuracy of any Contact Quality Monitoring or "NESSY" system used in an electrosurgical generator today. The present invention does not necessarily require the use of a split patient plate.

However, the present invention does require the use of a patient plate with a lossy dielectric region at its periphery and is not applicable to standard resistive or capacitive plates. Nonlimiting examples of a patient plate with a lossy dielectric region at its periphery include those biomedical electrodes disclosed in PCT Publication WO97/37719 (Netherly et al.).

One aspect of the present invention is the use of a lossy dielectric plate in conjunction with electronic circuitry. The Netherly patient plate is unique in that it does not pass current through its surface in the same way at all points of its lossy dielectric surface.

At the corners and the very outer border of the lossy dielectric surface, the current emerging from the patient (or introduced to a patient in the case of a stimulating or pacing electrode) is forced to pass through the lossy dielectric layer in a "more capacitve than resistive" way.

This lossy dielectric current flow results in a phase angle of that current flow being shifted from 0° to a negative number between 0° and −90°. In the center of the plate, the current is passed through in a totally resistive manner (like any other patient plate) and the phase angle is 0°.

Another aspect of the present invention is the use of the following equation to determine the total phase angle ($\Theta_{Total}$) of current flow, which is equal to the sum of the phase angle of the current flow passing through the lossy dielectric area and the phase angle of the current passing through the bare metal area of the electrode surface near the center of the plate, as seen in Equation I.

$$\Theta_{Total} = [\Theta_{Lossy\ Dielectric} * (Area_{Lossy\ Dielectric}/Area_{Total})] + [\Theta_{Bare\ Metal} * (Area_{Bare\ Metal}/Area_{Total})] \quad \text{I}$$

Thus, if the relative area of the bare metal and lossy dielectric contacting the patient changed, there would be a net change of the phase angle of the total current flow.

Using the Netherly Patient Plate with coverage of lossy dielectric material from portions of the perimeter inward, and preferably at the corners and edges of the electrical conductor, there is no way that the plate can be peeled up from any direction while keeping the ratio of bare metal area to lossy dielectric area the same.

In other words, the measure of change of phase angle over change in time is independent of any other parameter or property of the biomedical electrode, because electronic circuitry in the biomedical instrumentation can measure $\delta\Theta/\delta t$ without regard to any other function, property, or parameter of the patient plate. Further the biomedical instrumentation can be calibrated to measure any amount of $\delta\Theta/\delta t$ before an alarm is sounded.

Therefore, by monitoring the phase angle of current flow through any biomedical electrode over time, one can determine whether contact between the biomedical electrode and skin of a patient has changed. While any change in direct contact is not as critical for monitoring biomedical electrodes where any contact could be enough to receive faint electrical signals from the patient, any change in direct contact is critical for any biomedical electrode that requires the delivery of electrical current to a patient or receives from the patient electrical current delivered to the patient in another location.

Another aspect of the present invention is the use of any geometric configuration of electrical conductor on a biomedical electrode, so long as a portion of the electrical conductor is covered with a lossy dielectric material. Thus, using the equation above, one need not configure a biomedical electrode to have two or more electrical conductors nor need one use either a CQM or NESSY system that relies on differences in current flow between two or more electrical conductors on the surface of the biomedical electrode. The method of the present invention pertains to a split conductor patient plate or a solid conductor patient plate equally well. Therefore, manufacturing and performance economies of scale can be achieved regardless of the electrical conductor geometry.

A feature of the present invention is that, if one were to pass a stream of current through a lossy dielectric Netherly patient plate and monitor the phase angle, that phase angle should change if any portion or the periphery of the plate were lifted. In all cases, a drop in phase angle should be observed because the area being lifted from any edge would always have more lossy dielectric coating than bare metal lifted.

An advantage of the present invention is that a clearly superior method of biomedical electrode lift from skin of a patient, because the most likely source for lift to start would be at the corners of the electrode, and this is precisely where the lossy dielectric coating on an electrical conductor of a Netherly patient plate is located.

Moreover, another advantage of the present invention is the ability of monitoring lift of a solid, single conductor biomedical electrode, and that this lift could be detected regardless of which way the electrode begins to lift.

Thus, the invention can be expressed in a variety of ways: A method of detecting loss of contact between a biomedical electrode and skin of a patient, comprises the steps of detecting a shift in phase angle between electrical and magnetic components of an alternating current and sounding an alarm when the shift exceeds a predetermined amount. A method of detecting lift off of a biomedical electrode from skin of a patient also comprises the steps of measuring lift off using the equation:

$$\Theta_{Total} = [\Theta_{Lossy\ Dielectric} * (Area_{Lossy\ Dielectric}/Area_{Total})] + [\Theta_{Bare\ Metal} * (Area_{Bare\ Metal}/Area_{Total})]$$

and sounding an alarm when $\delta\Theta/\delta t$ exceeds a predetermined amount. A method of determining the amount of skin contact between a biomedical electrode and skin of a patient, comprises measuring change of phase angle over change in time of an energized biomedical electrode and sounding an alarm when change of phase angle over change in time exceeds a predetermined amount.

The invention also comprises an apparatus for detecting loss of contact between a biomedical electrode and skin of a patient, comprising a biomedical electrode having an electrical conductor having at least a portion thereof having lossy dielectric properties and means for detecting when a change in phase angle over change in time exceeds a predetermined amount.

Further features and advantages of the invention become apparent using the following drawings to describe the embodiments.

BRIEF DESCRIPTION OF DRAWINGS

The reference numerals refer to like parts in the several views, wherein.

Embodiments of Invention

Figure 1:
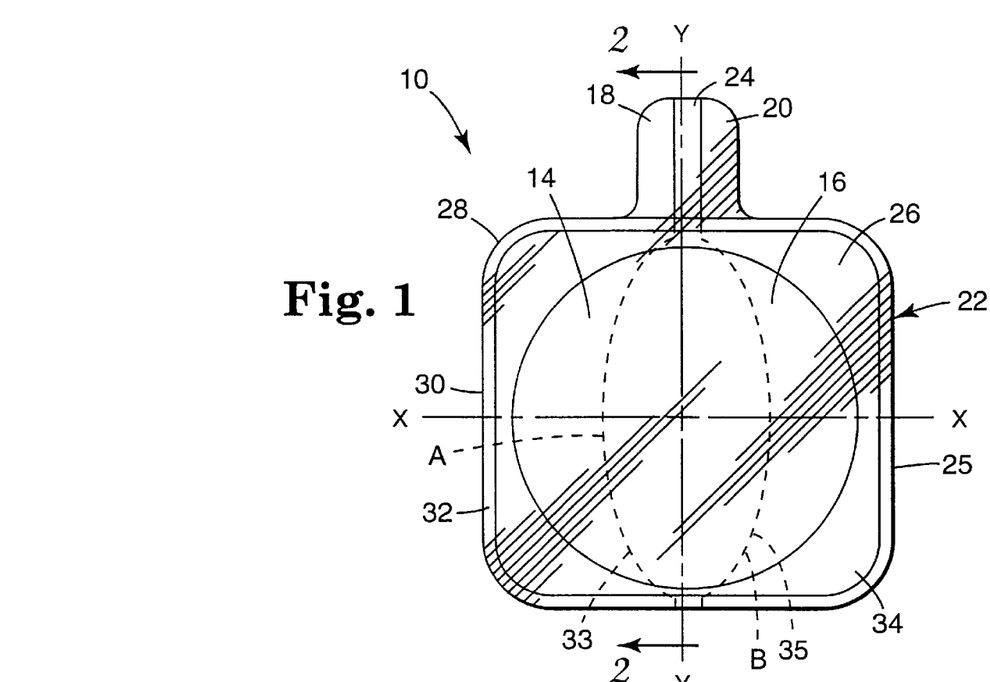
FIG. 1 is bottom perspective view according to one presently preferred embodiment of the dispersive electrode of the present invention.

FIG. 1 shows a bottom perspective view of the dispersive electrode "patient plate" 10. The upper surface of the electrode 10, which is on the far side in this bottom view, can be a flexible and conformable electrically non-conductive backing 12. At least one conductor plate is needed for electrical contact with the body of a patient. In this embodiment, two conductor plates 14 and 16 are present along a longitudinal axis Y—Y matching Section line 2—2, adjacent to, and can be adhered to, the electrically non-conductive backing 12. Two separate conductor plates are preferred because of their usefulness with contact quality monitoring ("CQM") circuitry because the impedance between the conductor plates 14 and 16 is measured by the above mentioned CQM circuits.

Each of the two conductor plates 14 and 16 has an extended tab 18 and 20, respectively, extending away from the body contact portion 22 of the electrode 10 for attachment of a cable assembly which connects the electrode 10 to an electrosurgical generator (not shown). When only one conductor plate is present on backing 12, there is only one extended tab. In order to provide more support for the conductor plates 14 and 16, and especially for their respective tabs 18 and 20, a non-conductive support layer 24 can be laminated to the conductor plates. More preferably, the support layer is not needed if manufacturing techniques can be refined.

The region adjacent the exterior edge 25 of the body contact portion 22 of the electrode 10 is covered with a layer 26 of a lossy dielectric material. In the embodiment of FIG. 1, the width of the layer 26 of a lossy dielectric material is widest at the corners 28, and narrowest along the edge 30 midway between the corners. As presently understood, this arrangement of the layer 26 serves best to reduce edge effect at the corners 28 of the dispersive electrode. Further explanation of the use of a lossy dielectric material can be found in PCT Publication WO 97/37719 (Netherly et al.).

Preferably, the entire body contact portion 22 of electrode 10 is covered with a field 32 of hydrophilic, ionically conductive, pressure sensitive adhesive for simplicity of manufacturing. Many compositions suitable for use for the field 32 of conductive adhesive are transparent, or at least translucent, and have been depicted that way in FIG. 1 for convenience in providing an explanatory drawing. The field 32 of adhesive serves the purpose of adhering the electrode 10 to the body of the patient. When the field 32 is adhesive that is ionically conductive, as it should be for those portions of field 32 contacting plates 14 and 16, the field also has the purpose of transferring the electrosurgical current between the body of the patient and the electrode for electrosurgical currents and between the electrode and the body for phase angle analysis according to the present invention.

Each of conductor plates 14 and 16 has an interior edge, 33 and 35 respectively, along the longitudinal axis Y—Y as seen in FIG. 1. Each of edges 33 and 35, or one of them, can be parallel, curvilinear or otherwise non-parallel to the opposing edge in a manner which creates a concave-inward indent relative to the longitudinal axis Y—Y. Preferably, both edges 33 and 35 have curvilinear geometries relative to the longitudinal axis, resulting in a double concave-inward indent symmetrical about the longitudinal axis. More preferably, the double concave-inward indent is also symmetrical about an axis orthogonal to the longitudinal axis, where the second axis is a latitudinal axis X—X substantially equidistant from edges of the body contact portion 22 orthogonal to the longitudinal axis. Most preferably, as seen in FIG. 1, at the point where longitudinal axis Y—Y and latitudinal axis X—X cross orthogonally, the non-conductive gap between edges 33 and 35 is maximal.

It will be seen that at point A which is away from the outside edge 25 of the body contact portion 22 of biomedical electrode 10, the minimum distance separating the conductive plates 14 and 16 is substantially greater than the minimum distance separating the conductive plates at a point B nearer the outside edge of the body contact portion.

Figure 2:
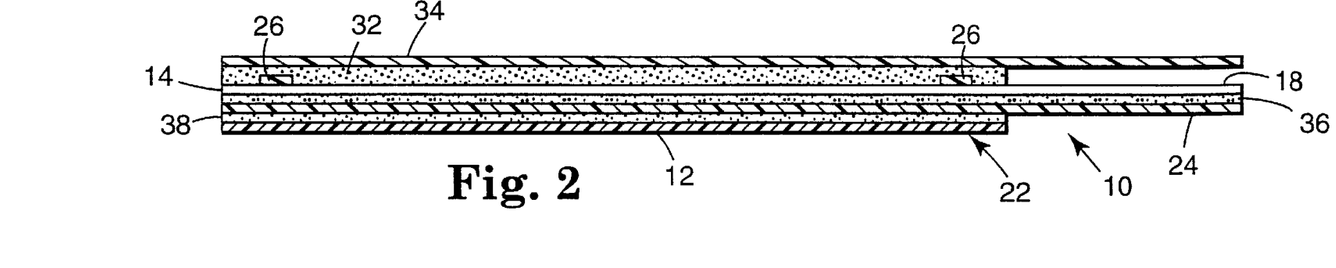
FIG. 2 is a cross-section view which is taken along section lines 2—2 in FIG. 1.

FIG. 2 shows a cross-section view of the electrode shown in FIG. 1, taken along section lines 2—2. In this view, a release liner 34 is shown adhered to the field 32 of hydrophilic adhesive. In those portions of electrode 10 where adhesive field 32 contacts one or more conductive plates 14 and 16, the adhesive field 32 is also ionically conductive. This release liner 34 protects the adhesive during shipping and handling and is removed just prior to use. In this view a layer of adhesive 36 is seen adhering the support layer 24 to conductor plate 14 and its extended tab 18. Another layer of adhesive 38 is provided for adhering the electrically non-conductive backing 12 to the other side of the support layer 24.

Electrically non-conductive backing

Electrically non-conductive backing 12 can be electrically insulative, and preferably is very conformable to the various contours of the mammalian body. Many materials can be used for this purpose, as will be apparent to those skilled in the art. In one presently preferred embodiment, a closed-cell foam is considered particularly suitable. One such material is commercially available as Volara brand foam from Voltek, Inc. of Massachusetts. Another is commercially available as a laminate of nonwoven polypropylene and low density polyethylene backing from Milliken of Spartanburg, S.C. The electrically non-conductive backing can have a thickness ranging from about 0.75 mm (0.03 inch) to about 1.5 mm (0.06 inch), and preferably 1.0 mm (0.04 inch).

Conductor plates and support layer

The conductor plates 14 and 16 are conveniently made from metal, preferably in the form of a foil, a metal-containing or graphite-containing coated ink or paint, or a vapor coated metal, and most preferably, aluminum foil. If a support layer 24 is not being used, a thickness of about 0.08 mm (0.0003 inch) is considered preferred. If a support layer 24 is being used, the metal foil or vapor coated metal can be thinner because of the support provided by the support layer. A suitable support layer 24 can be made from polyethylene terephthalate (PET) film, conveniently approximately 0.05 mm (0.002 inch) thick. This allows the aluminum layer to range in thickness between about 0.0075 mm (0.0003 inch) to about 0.025 mm (0.001 inch) and preferably 0.012 mm (0.0005 inch) or allows vapor coated metal to have a minimum thickness of about 1000 Angstroms. An example of vapor coated metal on a substrate is found in PCT Publication No. WO 94/26950.

Hydrophilic adhesive

Each of the hydrophilic adhesives useful in the present invention should be biocompatible with mammalian skin and can be formulated in both ionically conductive and non-conductive embodiments. The ionically conductive adhesives are useful in contact with both mammalian skin and conductor plates 14 and 16. The non-conductive adhesives can be used beyond the perimeter of the conductor plates 14 and 16.

Preferably, if expense of a single field 32 of hydrophilic, ionically conductive, biocompatible, pressure sensitive adhesive is not greater than the expense during manufacturing of applying two different types of adhesive to comprise field 32, then a single field is used even if ionic conductivity is not required to be present in the perimeter section of field 32 not contacting conductor plates 14 and 16.

Nonlimiting examples of hydrophilic adhesives useful in connection with the present invention include those compositions disclosed in U.S. Pat. Nos. 4,524,087 (Engel); 4,539,996 (Engel); 4,848,353 (Engel) and 5,133,356 (Bryan et al),; 5,225,473 (Duan); 5,276,079 (Duan et al); 5,338,490 (Dietz et al); 5,362,420 (Itoh et al); 5,385,679 (Uy et al); copending and coassigned applications PCT Publication Nos. WO 95/20634 and WO 94/12585; and PCT Patent Application Ser. Nos. US95/17079 (Docket No. 51537PCT6A); US95/16993 (Docket No. 51290PCT8A); and US95/16996 (Docket No. 48381PCT1A). Further non-limiting examples of hydrophilic adhesives that do not have ionically conductive properties but would be useful for the perimeter section of field 32 include U.S. Pat. Nos. 4,871,812 and 5,407,717 (both Lucast et al.); 4,981,903 and Re 34,958 (both Garbe et al.); 5,009,224 (Cole); 5,232,838 (Nelson et al.); and 5,270,358 (Asmus); PCT Publication WO 95/27016; and adhesives commercially available from the Medical Specialties Department of 3M Health Care, 3M Company, St. Paul, Minn.

Release liner

Release liner 34 can be any construction suitable for protecting the conductive adhesive 32 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Adhesive layers

In some presently preferred embodiments, adhesive layers 36 and 38 may be used for holding other components of the electrode 10 together. Nonlimiting examples suitable adhesives 6 and 38 include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935.

Lossy dielectric layer

The layer 26 of lossy dielectric material has the performance parameters identified above in association with the ultimate performance of electrode 10 to minimize the maximum rise in temperature of tissue of a patient during electrosurgical procedures.

The lossy dielectric layer 26 can occupy an area of the body contact portion 22 ranging from about 5% to about 70% and preferably from about 40% to about 60%. The percentage of area of body contact portion occupied by layer 26 determines two variables in the equation useful in the present invention.

The lossy dielectric layer 26 can be made from a material and be applied in a non-uniform thickness to result in an electrical impedance gradient from the center of the body contact portion 22 to the exterior edge 25 ranging from about 30% to about 90% of the maximum impedance at exterior edge 25, and preferably from about 50% to about 70% of the maximum impedance at exterior edge of body contact portion 22.

The layer 26 can have a maximum impedance/area at the exterior edge 25 of the body contact portion 22 of the electrode 10 ranging from about 0.387 $\Omega/129$ cm$^2$ to about 20 $\Omega/129$ cm$^2$ and preferably ranging from about 1 $\Omega/129$ cm$^2$ to about 8 $\Omega/129$ cm$^2$, as determined by use of a Schlumberger 1260 spectrum impedance analyzer, operating at a frequency of 500 KHz and a constant voltage of 60 mV (RMS), and subjected to a nulling file to subtract out the effects of leadwires, connecting clips, and test fixture. A dispersive electrode of approximately 129 cm$^2$ (20 in$^2$) is the approximate size of most commercially available dispersive electrodes.

The layer 26 can have a resistance component per unit area (R/area) of the complex impedance Z of from about 0.4 $\Omega/129$ cm$^2$ to about 5 $\Omega/129$ cm$^2$ at exterior edge 25 on the dispersive electrode 10. Preferably, the layer 26 can have a resistance component per unit area ranging from about 0.5 $\Omega/129$ cm$^2$ to about 1.4 $\Omega/129$ cm$^2$. These values were determined as done for the maximum impedance per unit area.

The layer 26 can have a reactance component per unit area (X/area) of the complex impedance of from about $-0.5$ $\Omega/129$ cm$^2$ to about $-16$ $\Omega/129$ cm$^2$ at exterior edge 25 on the dispersive electrode 10. Preferably, the layer 26 can have a reactance component per unit area ranging from about $-2$ $\Omega/129$ cm$^2$ to about $-10$ $\Omega/129$ cm$^2$, using the same testing method as above for resistance per unit area and impedance per unit area.

The layer 26 can have a $\tan \delta$ ranging from about 0.14 to about 1.7 at exterior edge 25 on the electrode 10, when measured at 500 KHz and a signal amplitude of 60 mV (RMS). Desirably, the $\tan \delta$ can range from about 0.2 to about 1.0 at exterior edge 25 on the electrode 10, when measured at 500 Hz and a signal amplitude of 60 mV (RMS). Preferably, the $\tan \delta$ ranging from about 0.2 to about 0.7 at exterior edge 25 on the electrode 10, when measured at 500 Hz and a signal amplitude of 60 mV (RMS).

Layer 26 can be made from any lossy dielectric material that can be applied to body contact portion 22 and provide the performance parameters identified above for layer 26.

Layer 26 can be formed from an ink or paint on body contact portion 22 according to electrode manufacturing techniques known to those skilled in the art. It has been found particularly convenient to provide this material in the form of a paint, which can then be screen printed or sprayed in an appropriately shaped pattern onto the electrode 10 at the proper time during its fabrication. Oil-based enamels, commercially available as Cat. nos. 7776, 7790, 7730, 7727, and 7715 from Rust-oleum Corp. of Vernon Hills, Ill. are considered particularly suitable. Inks such as Summit UVII 300, UVII 800, and UVII 801 white inks, from Summit, Inc. of North Kansas City, Mo. and Werneke Ultrafuse UFR Green, # UFGUB0008 from Werneke, Inc. of Plymouth, Minn. can also be used. Additional information on the use of a lossy dielectric layer to reduce the heating caused by edge effect can be found in PCT Publication WO 97/37719.

Method of Making Electrodes

Electrode 10 can be made using conventional tab/pad style electrodes as described in U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.). Generally, multiple layered electrode 10 can be assembled from rolls of starting materials for insulative electrically non-conductive backing 12, upon which is applied conductor plates 14 and 16, upon which is coated paints or inks to form lossy dielectric layer 26, upon which is coated or cured field 32 of hydrophilic, ionically conductive pressure sensitive adhesive. Alternatively, a sheet of lossy dielectric material of a desired geometrical shape can be laminated onto conductor plates 14 and 16.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and 5,702,753 (Yasis et al); and U.S. Pat. No. 5,352,315 (Carrier et al.).

Method of Monitoring Phase Angles

Any electronic method suitable for "real time" monitoring of phase angles in an electrical circuit is acceptable for use in the present invention. Because of the consistent advances in electronics, no one manner of monitoring of phase angles can be identified as clearly superior to another. However, several known methods can be outlined as presently suitable for use in the present invention.

Electronics for the present invention can rely on software, hardware, or both to achieve a monitoring of phase angles of current flow of various portions of a biomedical electrode connected to both biomedical instrumentation and the skin of a patient.

Nonlimiting examples of ways to monitor phase angles of current flows using hardware include various embodiments of analog to digital (A/D) signal conversion, analog multipliers, counters, phase locked loops, zero-crossing detectors, and combinations thereof.

One criterion to selection of a way to monitor phase angles of current flows is the time resolution required to determine the shifts in the phase angle. Of known ways to monitor phase angles, the use of zero-crossing detectors is presently preferred for the present invention. As A/D converters sample rates increase beyond 2 giga samples/sec., this method is preferred.

Nonlimiting examples of ways to monitor phase angles of current flows using software include A/D conversion-algorithm measurement. Time resolution can vary according to the needs of those skilled in the art, such as the change in phase angle required to indicate lift off of a plate edge. Using A/D conversion, the maximum sample period is given by the equation II:

$$T_{s,max} = (1/v)/(360°/\Theta) \qquad \text{II}$$

which also expresses the sampling period is determined by the required angular resolution to determine alarming phase angle shift, divided by the CQM frequency multiplied by 360. An example of use of this equation II appears in Table I for angular resolutions of 0.1 and 0.5 degrees in $\Theta$.

TABLE 1

| Freq. (v*1000) | $T_s$ = 0.1 (nanosecs.) | $T_s$ = 0.5 (nanosecs.) |
| --- | --- | --- |
| 100 | 2.8 | 14 |
| 150 | 1.9 | 9.5 |
| 200 | 1.4 | 7.0 |
| 250 | 1.1 | 5.5 |
| 300 | 0.93 | 4.7 |
| 350 | 0.79 | 4.0 |

TABLE 1-continued

| Freq. (v*1000) | $T_s$ = 0.1 (nanosecs.) | $T_s$ = 0.5 (nanosecs.) |
| --- | --- | --- |
| 400 | 0.69 | 3.5 |
| 450 | 0.62 | 3.1 |
| 500 | 0.56 | 2.8 |

Thus, for a 0.1 nanosecs. (ns) resolution at 500,000 HZ, an acceptable time resolution must be less than about 0.56 ns. Fast sampling (2 Giga samples per second) analog to digital (A/D) converters are state of the art in digital oscilloscopes. At 2 Gsa/sec, a signal is sampled every 0.5 nanosecond. To resolve a pure sine wave to one tenth degree accuracy at 500 KHz requires a sampling rate of 2 Giga samples per second or greater. This is at the high end of sampling scopes. If several periods of a CQM signal (cauterizing signal) have been captured, a digital signal processor (DSP) device or a microprocessor ($\mu$P) could compute, algorithmically, the average phase angle difference, $\Theta$, between the source signal, $v_{source}(t)$, and the CQM cauterizing signal, $v_{cauterize}(t)$, by using a discrete time Fourier transform (DTFT) of the CQM cauterizing signal, $v_{cauterize}(n)$ where $v_{cauterize}(n)$ is the discrete time sample of $v_{cauterize}(t)$.

Figure 3:
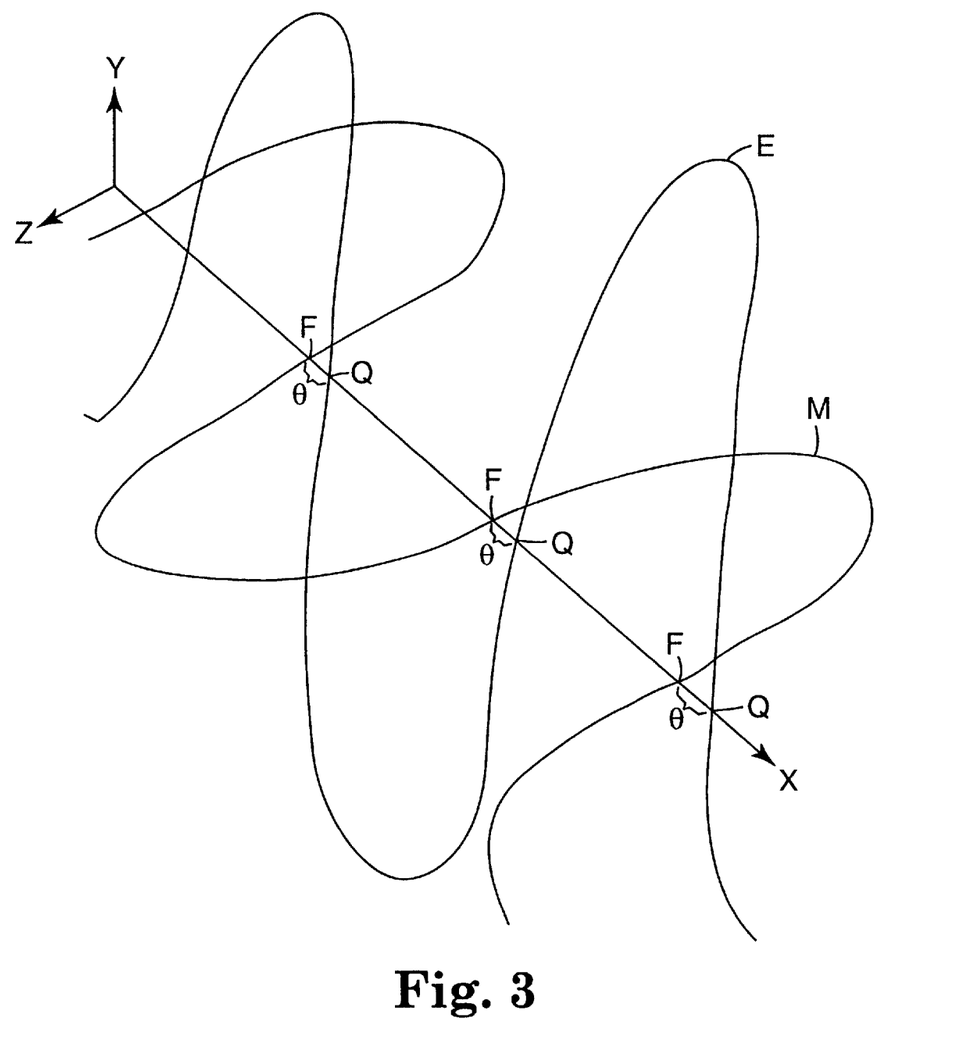
FIG. 3 is an illustration of the relationship between the electrical and magnetic components of an alternating current signal useful in the present invention.

This is done by the following. Assuming that the source and CQM cauterize signals are both voltages, AC coupled, defined by, respectively, in Equations III and IV:

$$v_{source}(t) = V_{source} \cos(\omega t + Q) \qquad \text{III}$$

and $$v_{cauterize}(t) = V_{cauterize} \cos(\omega t + F) \qquad \text{IV}$$

then the phase angle between the two signals ($\Theta=Q-F$) can be computed by the inverse tangent of the imaginary DTFT component over the real DTFT component of the cauterizing signal taken with respect to the source. FIG. 3 shows the difference between Q and F, where Q is the x intercept of the electrical wave (E) and F is the x intercept of the corresponding magnetic wave (M) orthogonal to the electrical wave.

Alternatively, the phase angle can be represented by equation V:

$$\text{phase angle} = \Theta = Q - F = \tan^{-1}\{IM(v_{cauterize}(n))/RE(v_{cauterize}(n))\} \qquad \text{V}$$

where IM (.) is the imaginary component and RE(.) is the real component of the discrete time cauterizing signal, $v_{cauterize}(n)$.

If a cauterizing machine incorporates a fast A/D converter to sample the current through the patient electrode, a 0.1° phase angle ($\Theta$) resolution at 500 KHz can be possible. This requires a A/D sampling rate of less than 0.56 ns according to Table 1 above. 0.5 nanosecond resolution would be possible. Factors to consider in this would be the cost of the A/D converter and the benefits of having a flexible method of computing phase angle, easily modified by software upgrades, not hardware retrofitting.

Alternatively, "equivalent time sampling" could be used. "Equivalent time sampling" uses the fact that a periodic signal is being used and that multiple cycles of the signal may be used to reconstruct the original signal, and hence the shift in phase angle $\Theta$. It is preferred that the equivalent time sampler have the ability to shift its sample interval in steps less than or equal to $T_{s,max}$.

The sampling of $v_{cauterize}(t)$ is triggered when $v_{source}(t)$ becomes greater than 0 volts. A single sample of $v_{cauterize}(t)$ is made at that time. One period later, when $v_{source}(t)$ becomes positive, the sampling of $v_{cauterize}$ is offset or delayed by $T_{s,max}$ and a sample is taken. One period later, the sample of $v_{cauterize}$ is offset by $(2*T_{S,max})$ This process continues until $v_{cauterize}(t)$ becomes greater than 0 volts. Using this method, repetitive sampling rates of $T_{s,max}$ are not required, only a sampling period of that of $v_{souce}(t)$ plus $T_s$, max offset.

Also the sampling of the entire period of $v_{cauterize}(t)$ is unnecessary, in that all the required information is gathered in the time immediately after $v_{source}(t)$ becomes positive to the time when of $v_{cauterize}(t)$ becomes positive. This reduces the digital memory requirements of the A/D conversion.

The shift in phase angle (Θ), computed in °, is solved by Equation VI:

$$\Theta = 360°[(Ts_{,max} * \text{no. of offsets})/Tv_{source}] \quad \text{VI}$$

It is preferred that the sampling of $v_{cauterize}(t)$ be controlled to within time increments of $Ts_{,max}$ as shown in Table 1 above.

The equivalent time sampling method incorporates electronic counters. In counting the offsets of Ts, an electronic counter or shift register can be used. Use of the counter in measuring Θ is not limited to the equivalent time sampling method. An alternative would be to use a fast counter or combination of counters that are triggered to start when the $v_{source}(t)$ becomes positive and stops when $v_{cauterize}(t)$ becomes positive. By counting the number of counts between the start and stop and multiplying by the period of the counters and using Equation VII:

$$\Theta = 360°[(Ts_{,max} * \text{counts}/Tv_{source}] \quad \text{VII}$$

Fast crystals are used in personal computers, with clock cycles much less than 5 ns.

Figure 4:
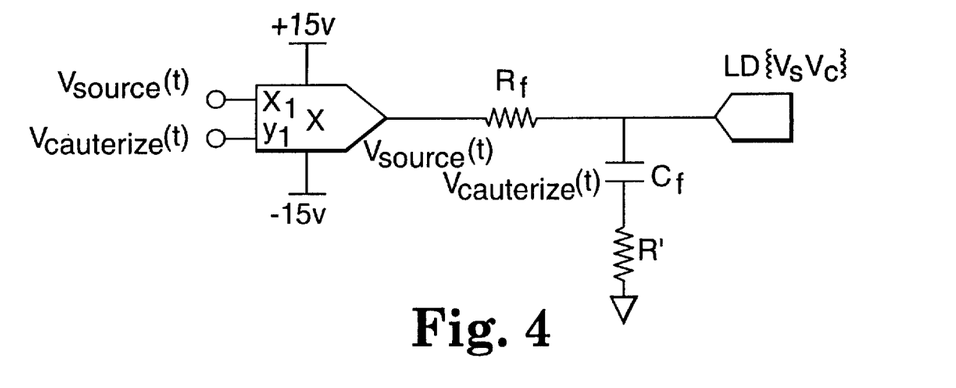
FIG. 4. is an electronic circuit diagram for one embodiment of the invention.

A direct approach is to do a hardware multiply of the two signals, $v_{source}(t)$ and $v_{cauterize}(t)$, as seen in FIG. 4. The hardware embodiment involves hardware circuitry and precludes algoritlun changes. Two signals are multiplied in hardware (using an MPY634 multiplier commercially available from Burr Brown of Tuscon, Ariz. USA or AD532 or AD534 multiplier commercially available from Analog Devices of Norwood, Mass., USA) using Equations III and IV above to yield Equation VIII $$v_{source}(t)v_{cauterize}(t) = 0.5 V_{source}V_{cauterize}\{\cos(Q-F)+\cos(2\omega t+Q+F)\} \quad \text{VIII}$$

When the low pass filter (whose high frequency cutoff is much less than 2ωt) is applied to the above (through a resistor-capacitor series connection or through an operation amplifier low pass filter or some other circuit), the high frequency component, cos (2ωt+Q+F) is filtered out to leave only $$LP\{v_{source}(t)v_{cauterize}(t)\} = 0.5 V_{source}V_{cauterize}\{\cos(Q-F)\} \quad \text{IX}$$

Thus if $V_{source}$ and $V_{cauterize}$ are accurately known, then the phase angle between the two signals can be computed using $$\Theta = Q-F = \cos^{-1}[2 LP\{v_{source}(t)v_{cauterize}(t)\}/(V_{source}V_{cauterize})] \quad \text{X}$$

One embodiment for determining the phase angle according to the above equations is the use of a hardware multiplier. The pertinent features from these devices are high bandwidth, high multiplier accuracy, and low noise. Potential devices are the multipliers identified above.

While the hardware (MPY634) to measure the phase angle may be relatively inexpensive, it requires an accurate measurement of both $V_{source}$ and $V_{cautcrize}$. This can also be done but is quite difficult in practice that a measurement error in 1.2% in the product of 0.5 $V_{source}*V_{cauterize}$ will give erroneous results of greater than a 1 degree phase shift (at 45 degrees). The situation requires more precision at about the 8 degree phase shift level (the phase shift numbers given in the RI). To compute the difference between 8.0 and 8.1 degrees, accuracy and precision is required as well as nulling out the impedance effects of cabling. To do so will require real-time precision signal conditioning in the cauterizing machine and precise nulling out or compensation of the phase shift of the cabling connecting the patient plates to the electrosurgical generator or cauterizing machine.

Another embodiment can use a phase locked loop device. Many phase locked loop devices provide phase detection. The utility of phase locked loop devices is not in phase locking but rather that many of these devices have an output indicating phase shift.

Another embodiment can use a zero-crossing detector. Zero crossing detectors are used in triggering and other embodiments.

Using fast analog comparators, one can measure $v_{source}(t)$ and can detect when it crosses zero volts ($v_{source-zero-cross}(t)$), assuming an AC coupling. Similarly, one can measure $v_{cauterize}(t)$ and can detect it when it crosses zero volts ($v_{cauterize-zero-cross}(t)$).

From these two zero crossing digital signals one can measure the time difference between the onset of the two pulses. This can be done in a variety of ways including, but not limited to integration of these AND'ed pulses. The benefit of this method is that there does not need to be an accurate, repetitive measurement of amplitudes of $v_{source}(t)$, $v_{cauterize}(t)$, $V_{source}$, and $V_{cauterize}$, but rather an accurate zero crossing detection which could be the average of many zero crossings. The measurement is more quickly moved to digital techniques which can be more accurate in mass production.

Figure 5:
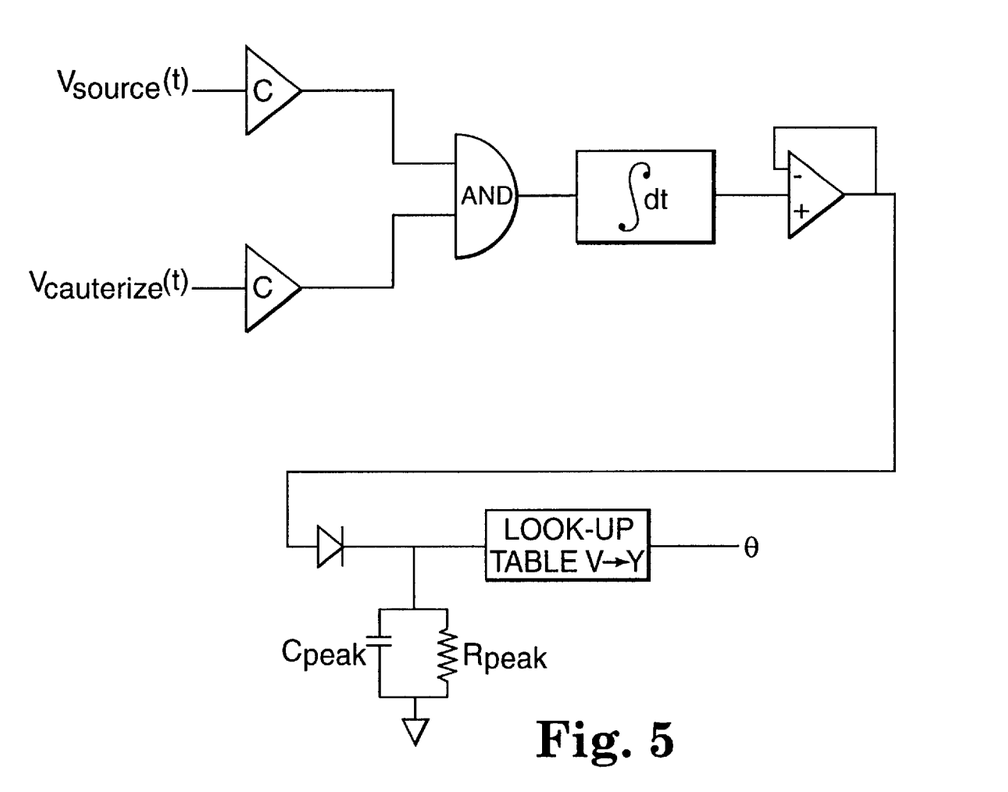
FIG. 5 is an electronic circuit diagram for another embodiment of the invention.

One embodiment, as seen in FIG. 5, to measure time difference can be using an integration of a resistor/capacitor (RC) circuit. If the product of R and C is smaller than the $T_{s,max}$ then the fast pulses will be integrated. This is input into a buffer with a low input bias current leakage. This potential is compared to a computer stored look-up table to map potential to the shift in phase angle Θ. One can feed these zero crossing signals into a fast AND gate which drives a parallel resistor (R) and capacitor (C). The parallel RC functions as an integrator of the signal out of the AND gate ($v_{and}(t)$), such that $$V_{RC} = \int V_{and}(t) \quad \text{XI}$$

This value is indicative of the phase relation between $v_{source}(t)$ and $v_{cauterize}(t)$. The product of RC (τ=RC) should be such that τ is much greater than the period of $v_{source}(t)$. If τ is judiciously selected, $v_{RC}(t_{peak})$ will hold its value between positive pulses while the RC of the intergrator detects fast pulses.

This method obviates the need to form accurate analog preamplification and detection, relying upon accurate zero-crossing detection in the pre-amp stage. This method does, however, require one accurate analog measurement of the potential output from the integrator and an zero cross detector of $V_{cauterize}$ and $V_{source}$.

Regardless of the method of detection of a change in Θ, an output of that change can be directed to a conventional electronic circuit that signals an alarm when the amount of change in Θ exceeds a predetermined amount. One skilled in the art can readily employ a myriad of conventional electronic circuits to generate an alarm, which can be visible, audible, or otherwise. Moreover, one skilled in the art can further electrically communicate the alarm condition to other circuitry of the biomedical instrumentation that drives the electrosurgery or other operation being performed on the patient. It is contemplated within the scope of this invention that once the conditions of an alarm are present, as detected according to the method of this invention, that any biomedical instrumentation can be adjusted or any medical personnel can be informed, in any way desired for the advancement of medical safety.

Usefulness of the Invention

Beyond the immediate utility to monitor lift of patient plates from skin of patients, this invention has a much broader application in other biomedical electrodes, or even beyond in other areas where additional information is desired about conduction across an interface.

For example, a biomedical electrode may be manufactured with a lossy dielectric coating located in certain areas that will "signal" whether those areas are effectively conducting electricity or have become disconnected in some way. The purpose of the lossy dielectric coating in such a biomedical electrode may not be to alter the current distribution in any way, but may simply serve as a way of "signaling" that certain areas of the electrode are indeed conducting electricity.

At the most fundamental level, this invention concerns the inducing of a phase shift in some fraction of an electrical current traveling across an interface, for the purpose of encoding information about the condition of that interface into the electrical current itself. It is important to note that this is accomplished without a change in frequency, voltage, or amperage and is done by the very simple means of introducing a lossy dielectric material at certain points in the interface. In today's environment of digital data, multiplexed data lines, and all the attendant available communications and electronics technology, adding additional information to a stream of electrons appears to be no great task.

Moreover, information can be transmitted electrically by varying the frequency or voltage or amperage of a stream of electrons, and more than one stream of information can be easily contained in the same stream of electrons with today's technology.

This invention provides a means of passing information about an electrical interface "downstream" with the bulk current flow passing across the interface, and for extracting this information at some later time by measuring the phase angle of the current flow. This is accomplished by relatively simple technical means of adding a coating of a material that shifts the phase angle of the current passing through it to discrete parts of the interface, without the use of any other circuit components whatsoever.

Because this invention employs the special properties of lossy dielectric components in an electrical interface, the invention uses a material that inhabit a curious "no man's zone" in that lossy dielectric surfaces are generally regarded as having the properties of a badly defective resistor or capacitor that is totally unusable for the purpose that either component is designed for. As such, this invention can be a novel adaptation of an electrical phenomena that had up until now been regarded as a failure mode of other common devices.

Biomedical electrodes of the present invention can be electrically connected to electrosurgical generators or cardiac stimulation devices to provide dispersive electrode connection or cardiac stimulation electrode connection, respectively. Electrosurgical generators are commonly available and known to those skilled in the art, such as devices marketed by Birtcher Medical Systems, Inc. of Irvine, Calif.; Aspen Surgical Systems, Inc. of Utica, N.Y.; and Valleylab, Inc. of Boulder, Colo. Cardiac stimulation devices for cardioversion, external pacing, and defibrillation are commonly available and known to those skilled in the art, such as devices marketed by Hewlett-Packard Corporation of McMinnville, Oreg.; Zoll Medical Corporation of Newton, Mass.; and Physiocontrol Corporation of Redmond, Wash. Any of these medical devices can be modified to include hardware and software embodiments of this invention to provide a measurement of the difference of phase angle to advantage according to this invention.

Embodiments of the invention are further described in the following examples.

EXAMPLE 1

An electrode was constructed according the following procedure. An electrode was constructed from a 129 $cm^2$cm (20 square inches) of Aluminum foil having corners with a radius of 2.54 cm. A layer of conductive adhesive was prepared according to the following procedure. Into a 300 gallon kettle equipped with overhead stirrer and a cooling jacket was charged 562.8 pounds (255.5 kg) acrylic acid, 1.4 pounds (636 grams) 2,2-dimethoxy-2-phenyl acetophenone, 2.8 pounds (1273 grams) 4-(2-hydroxyethoxy)phenyl-(2-hydroxy-2-methylpropyl)ketone, 1.12 pounds (508 grams) methylene bis(acrylamide), 1251.6 pounds (568.2 kg) glycerin, 2.8 pounds (1273 grams) guar gum, and 459.6 pounds (208.7 kg) deionized water. To the well stirred solution was charged 499.8 pounds (226.9 kg) 50% aqueous NaOH portionwise maintaining the batch temperture below 38° C. The hydroxide line was rinsed into the kettle with an additional 18 pounds (8.2 kg) deionized water and stirred for 30 minutes to yield coater-ready precursor. The precursor was coated onto the foil side of a polyester/aluminum foil laminate at 23 mil (0.6 mm) thick, overlaminated with a siliconized polyester liner, and passed through a curing chamber consisting of banks of fluorescent "black" lights, exposing the material to an intensity of 1.9 mW/sqcm and a total dose of 315 mJ/sqcm. The layer of conductive adhesive so prepared was then placed over the whole square of the electrically conductive surface.

A water-based vinyl primer was pattern-printed on the aluminum side of 246 cm wide, 0.13 mm aluminum foil/0.05 mm polyester laminate using a 550 line per 2.54 cm (lpi) anilox roll in a multi-station Flexographic printing press. The pattern consists of a 11.43 cm (4.5") square with an unprinted 8.1 cm (3.182") diameter circle inside the square whose center was also at the center of the square. A layer of UV curable, green acrylate ink (Werneke Ultrafuse UFR Green, # UFGUB0008 from Werneke, Inc. of Plymouth, Minn.) was pattern-printed using a 300 lpi anilox roll, over the primer on the 11.43 cm (4.5") square. At this print station, a 8.1 cm (3.382") diameter circle was left unprinted inside the square whose center is also at the center of the square. Then a second layer of the same ink was pattern-printed using a 200 lpi anilox roll, over the layer #1 of ink and primer on the 11.43 cm (4.5") square. During this printing, a 9.1 cm (3.582") diameter circle was left unprinted inside the square whose center was also at the center of the square. Then a third layer of the same ink was pattern-printed using a 200 lpi anilox roll, over the layer #2 and layer #1 of that ink and primer on the 11.43 cm (4.5") square. During this final printing, a 9.6 cm (3.782") diameter circle was left unprinted inside the square whose center was also at the center of the square.

One electrode so prepared was placed on a human anterior thigh, and for comparison, a Model No. 7149 patient plate (Minnesota Mining and Manufacturing Company, St. Paul, Minn., USA) was placed on the posterior surface of the same thigh. The tabs of the two plates were then hooked up to a Schlumberger 1260 Spectrum Impedance Analyzer, and the Schlumberger instrument was programmed to measure impedance and phase angle once per second for 3 minutes, at a frequency of 500 KHz and a current level of 60 mA.

During this period the 4 corners of the test electrode were gently lifted in order, and then pressed back down in the reverse order. The results are shown graphically in FIG. 6, and a clear "stair step" effect in change in phase angle can be seen as each corner is lifted and pressed down again.

Figure 6:
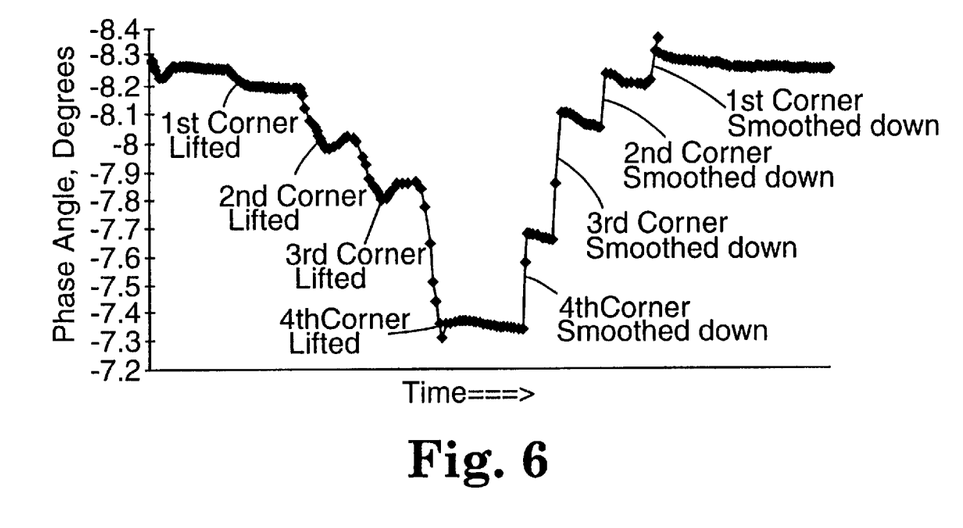
FIG. 6 is a graph showing the effect of lift-off of a biomedical electrode using the method of the invention.

As can be seen in FIG. 6, the effect of lifting all 4 corners of the test electrode is cumulative as it would be expected to be, since as the corners are consecutively lifted the ratio between the lossy dielectric area and bare metal area becomes larger.

Based on this example, then, a clear, reproducible, and measurable relationship is shown between the lift of a solid, lossy dielectric patient plate and the phase angle of the current flow passing through that plate as a whole. As one or more of the corners is lifted off, the phase angle "drops" from a larger negative value to a smaller negative value. It should be noted that the lift of one corner constituted less than 10% lift of the total conductive surface area, and that this lift was in an area that could not be detected by any CQM system in existence today even if a split plate were used.

This example shows that the method of the present invention is an unexpected advance over conventional Contact Quality Monitoring of patient plates while using a much simpler design without split electrical conductors. By monitoring the phase angle of the current passing through the electrode, lift along any edge or corner can be monitored without respect to the shape or geometry of the plate, and the placement of the electrode on the patient is also totally irrelevant so long as contact remains continuous.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A method of determining the amount of skin contact between a biomedical electrode and skin of a patient, comprising the steps of:
    (a) measuring change of phase angle over change in time ($\delta\Theta/\delta t$) of an energized biomedical electrode in contact with a patient's skin;
    wherein the measuring step uses the equation:
    $\Theta_{Total}=[\Theta_{Lossy\ Dielectric}*(Area_{Lossy\ Dielectroc}/Area_{Total})]+[\Theta_{Bare\ Metal}*(Area_{Bare\ Metal}/Area_{Total})]$; and
    (b) sounding an alarm when $\delta\Theta/\delta t$ exceeds a predetermined amount; $\delta\Theta/\delta t$ being indicative of the amount of skin contact between a biomedical electrode and the patient's skin.

2. The method of claim 1, wherein the measuring step uses software, hardware, or both to achieve a monitoring of phase angles of current flow of various portions of the energized biomedical electrode connected to both biomedical instrumentation and the skin of a patient.

3. The method of claim 2, wherein the measuring step uses software including an A/D conversion algorithm measurement wherein the maximum sample period is given by the equation:

$$T_{s,max}(1/v)/(360°/\Theta).$$

4. The method of claim 3, wherein the phase angle is represented by the equation:

$$phase=\Theta=Q-F=\tan^{-1}\{IM(v_{cauterize}(n))RE(v_{cauterize}(n)\}$$

where IM (.) is the imaginary component and RE(.) is the real component of the discrete time cauterizing signal, $v_{cauteize}(n)$.

5. The method of claim 2, wherein the measuring step uses hardware circuitry.

6. The method of claim 5, wherein the hardware circuitry multiplies two signals to yield the following equation:

$$\Theta=Q-F=\cos^{-1}[2\ LP\{v_{source}(t)v_{cauterize}(t)\}/V_{source}V_{cauterize})],$$

wherein Q is the x intercept of electrical wave (E) and F is the x intercept of the corresponding magnetic wave (M) orthogonal to the electrical wave; wherein $LP\{v_{source}(t)\ v_{cauterize}(t)\}$ is an amount using a low pass filter of the two signals $v_{source}(t)\ v_{cauterize}(t)$ being multiplied and ($V_{source}\ V_{cauterize}$) are known values of the voltages of the source signal and the cauterizing signal.

7. The method of claim 5, wherein the hardware circuitry is a phase locked loop device.

8. The method of claim 5, wherein the hardware circuitry is a zero-crossing detector.

9. The method of claim 5, wherein the hardware circuitry measures time difference using an integration of a resistor/capacitor circuit using the following equation:

$$V_{RC}=\int v_{and}(t)$$

wherein the equation uses zero crossing signals into a fast AND gate which drives a parallel resistor and capacitor.

10. The method of claim 1, wherein the alarm is visible or audible.

11. The method of claim 10, wherein the alarm is electrically connected to biomedical instrumentation that drives electrosurgery.

12. An apparatus for detecting loss of contact between a biomedical electrode and skin of a patient, comprising:
    (a) a biomedical electrode having an electrical conductor wherein at least a portion thereof has a layer of lossy dielectric material in electrical contact with both biomedical instrumentation and the skin of a patient; and
    (b) means for detecting when a change in phase angle over change in time ($\delta\Theta/\delta t$) exceeds a predetermined amount; wherein the means for detecting is electrically connected to the biomedical electrode: and
    wherein means for detecting uses the equation:
    $\Theta_{Total}=[\Theta_{Lossy\ Dielectric}*(Area_{Lossy\ Dielectric}/Area_{Total})]+[\Theta_{Bare\ Metal}*(Area_{Bare\ Metal}/Area_{Total})]$ to sound an alarm when $\delta\Theta/\delta t$ exceeds the predetermined amount; and wherein $\delta\Theta/\delta t$ uses voltage signals of a source signal $v_{source}$ and a cauterizing signal $v_{cauterize}$.

13. The apparatus of claim 12, wherein the biomedical electrode has a body contact portion that includes the electrical conductor and the layer of lossy dielectric; and wherein the electrical conductor comprises at least two conductor plates.

14. The apparatus of claim 12, wherein each of the at least two conductor plates has an extended tab extending away from the body contact portion.

15. The apparatus of claim 13, wherein the body contact portion further comprises a field of pressure sensitive adhesive.

16. The apparatus of claim 15, wherein the field of pressure sensitive adhesive is ionically conductive.

17. The apparatus of claim 13, wherein the at least two conductor plates have interior edges having curvilinear geometries relative to a longitudinal axis of the biomedical electrode.

18. The apparatus of claim 13, wherein the at least two conductor plates are made from metal-containing or graphic-containing coated ink or paint.

19. The apparatus of claim 13, wherein the layer of lossy dielectric material occupies an area of the body contact portion ranging from about 5% to about 70% defining an area percentage and wherein the area percentage determines two variable in the equation.

20. The apparatus of claim 17, wherein the layer of lossy dielectric material is applied in a non-uniform thickness to result in an electrical impedance gradient from the interior edge to an exterior edge of the body contact portion ranging from about 30% to about 90% of the maximum impedance at the exterior edge of the body contact portion.

* * * * *

UNITED STATES PATENT AND TRADEMARK OFFICE
CERTIFICATE OF CORRECTION

PATENT NO. : 6,171,304 B1
DATED : January 9, 2001
INVENTOR(S) : Samuel G. Netherly and Orlin B. Knudson Page 1 of 1

It is certified that error appears in the above-identified patent and that said Letters Patent is hereby corrected as shown below:

Column 2,
Line 49, "Tuibingen" should read -- Tubingen --.

Column 7,
Line 46, "6 and 38" should read -- 36 and 38 --.

Column 14,
Line 47, "246 cm" should read -- 24 cm --.

Column 15,
Line 56, "($Area_{Lossy\ Dielectroc}/Area_{Total}$)" should read -- ($Area_{Lossy\ Dielectric}/Area_{Total}$) --.

Column 16,
Line 11, "(n))RE" should read -- (n))/RE --.
Line 21, "/$V_{source}V_{cauterize}$)]" should read -- / $V_{source}V_{cauterize}$)] --

Signed and Sealed this

Eleventh Day of December, 2001

Attest:

NICHOLAS P. GODICI
Attesting Officer
*Acting Director of the United States Patent and Trademark Office*